(12) United States Patent
Lee et al.

(10) Patent No.: US 7,465,816 B2
(45) Date of Patent: Dec. 16, 2008

(54) PRODUCTION OF TETRAHYDROFURAN FROM 1,4-BUTANEDIOL

(75) Inventors: Eun Ku Lee, Gyeonggi-Do (KR); Yong Ho Baek, Gyeonggi-Do (KR)

(73) Assignee: Hyosung Corporation, Seoul (KR)

( * ) Notice: Subject to any disclaimer, the term of this patent is extended or adjusted under 35 U.S.C. 154(b) by 0 days.

(21) Appl. No.: 11/805,447

(22) Filed: May 23, 2007

(65) Prior Publication Data

US 2008/0161585 A1    Jul. 3, 2008

(30) Foreign Application Priority Data

Dec. 29, 2006    (KR) .................. 10-2006-0138714

(51) Int. Cl.
*C07D 307/08* (2006.01)
(52) U.S. Cl. .................. 549/509; 502/217; 502/349
(58) Field of Classification Search .................. 549/509; 502/217, 349
See application file for complete search history.

(56) References Cited

U.S. PATENT DOCUMENTS

| | | | |
|---|---|---|---|
| 4,136,099 A | 1/1979 | Smith | |
| 4,665,205 A | 5/1987 | Yamada et al. | |
| 6,204,399 B1 | 3/2001 | Schoedel et al. | |

FOREIGN PATENT DOCUMENTS

JP    61-126080    6/1986

OTHER PUBLICATIONS

Sohn et al. "Preparation of a new solid superacid catalyst, zirconium sulfaic supported on γ-alumina and activity for acid catalysis," Catalysis Today, vol. 87, 2003, pp. 219-226.

*Primary Examiner*—Bernard Dentz
*Assistant Examiner*—David E Gallis
(74) *Attorney, Agent, or Firm*—Hamre, Schumann, Mueller & Larson, P.C.

(57) ABSTRACT

Provided is a method for the production of tetrahydrofuran (THF) from 1,4-butanediol (BDO) using a zirconium sulfate ($Zr(SO_4)_2 \cdot nH_2O$) catalyst. The method of the present invention can achieve high-yield production of tetrahydrofuran via a simple and low-risk production process by dehydration of 1,4-butanediol in the presence of a zirconium sulfate catalyst.

5 Claims, 1 Drawing Sheet

PRODUCTION OF TETRAHYDROFURAN FROM 1,4-BUTANEDIOL

BACKGROUND OF THE INVENTION

This non-provisional application claims priority under 35 U.S.C. § 119(a) on Korean Patent Application No. 10-2006-0138714 filed on Dec. 29, 2006, which is herein incorporated by reference.

1. Field of the Invention

The present invention relates to a method for producing tetrahydrofuran (THF) from 1,4-butanediol (BDO). More specifically, the present invention relates to a method for producing tetrahydrofuran in high yield from 1,4-butanediol using a zirconium sulfate $(Zr(SO_4)_2.nH_2O)$ catalyst.

2. Description of the Related Art

Tetrahydrofuran has been widely used in various fields including as a solvent of organic compounds or a starting material for polymer synthesis. Recently, use of tetrahydrofuran has gradually increased with finding its application as a starting material and an additive to synthetic polymers. Tetrahydrofuran has been produced by various processes.

Generally, tetrahydrofuran is obtained by dehydration of 1,4-butanediol or hydrogenation of furan. The dehydration of 1,4-butanediol is carried out by two steps including reacting 1,4-butanediol in the presence of an acid catalyst and then removing water from the water-containing reaction product, e.g. tetrahydrofuran. The yield of the process is determined by the performance of the acid catalyst used in the reaction, so research has continuously been required to develop effective catalysts for use in dehydration of 1,4-butanediol. U.S. Pat. No. 4,665,205 discloses a dehydration process of 1,4-butanediol using an inorganic acid catalyst such as sulfuric acid. However, the above process has problems that inorganic acid is dangerous to handle and the reactor is corroded by the inorganic acid.

Further, there are methods of producing tetrahydrofuran from 1,4-butanediol in the presence-of several acid catalysts, e.g. U.S. Pat. No. 6,204,399, Japanese Unexamined Patent Publication No. Hei 09-059191, U.S. Pat. No. 4,136,099, and Japanese Unexamined Patent Publication No. Sho 61-126080 disclose dehydration reactions of 1,4-butanediol using an alumina catalyst, a silica-alumina catalyst, an alumina-supported tungsten oxide catalyst, and a heteropolyacid catalyst, respectively. However, these methods also suffer from disadvantages associated with the activity and stability of the catalysts.

SUMMARY OF THE INVENTION

Therefore, the present invention has been made in view of the problems of the prior art and it is one object of the present invention to provide a safe and convenient high-yield method for producing tetrahydrofuran (THF) from 1,4-butanediol (BDO) using a zirconium sulfate $(Zr(SO_4)_2.nH_2O)$ catalyst.

BRIEF DESCRIPTION OF THE DRAWINGS

The above and other objects, features and other advantages of the present invention will be more clearly understood from the following detailed description taken in conjunction with the accompanying drawing, in which.

DETAILED DESCRIPTION OF THE PREFERRED EMBODIMENTS

Figure 1:
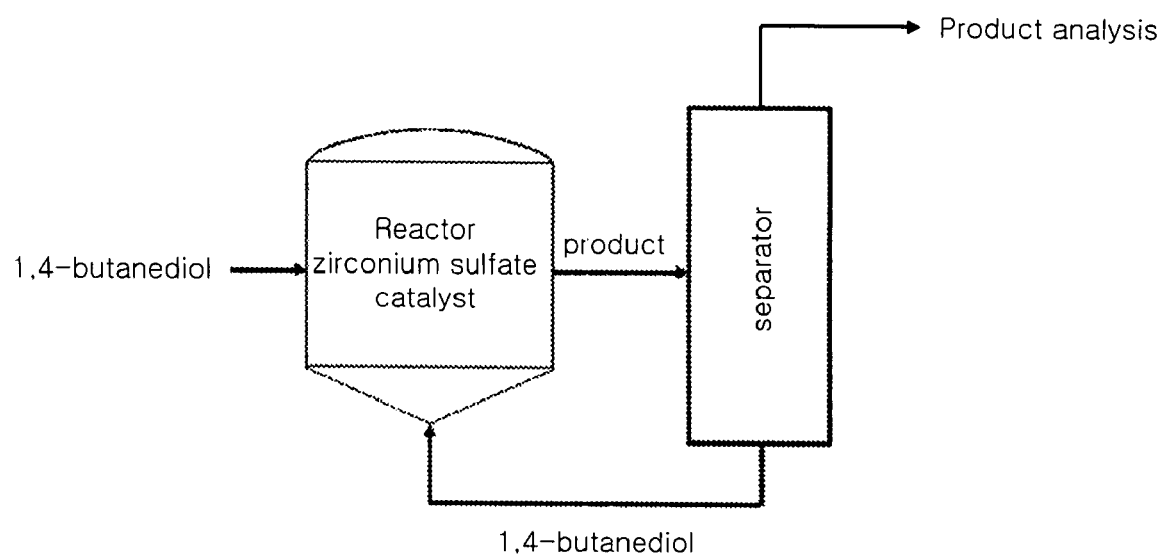
FIG. 1 is a schematic block diagram illustrating a production process of tetrahydrofuran (THF) by dehydration of 1,4-butanediol according to embodiments of the present invention.

The present invention will now be described in greater detail with reference to the accompanying drawing.

In one aspect, the present invention is directed to a method for production of tetrahydrofuran from 1,4-butanediol in the presence of a zirconium sulfate $(Zr(SO_4)_2.nH_2O)$ catalyst having a high-efficiency reaction activity.

The zirconium sulfate catalyst used in the embodiments of the present invention has high reaction activity and selectivity and has an excellent catalyst stability.

The zirconium sulfate catalyst is known as a solid super acid catalyst and has a surface area of 70 to 100 $m^2/g$ and a mesopore structure. In general, Lewis acid sites and Bronsted acid sites coexist on the surface of the zirconium sulfate catalyst and participate together in the reaction, thereby exhibiting synergistic effect,. Important properties of the zirconium sulfate catalyst such as strength and kind of the acid depends on a catalyst precursor, a doping process of sulfate and activation of the catalyst. In embodiments of the present invention, the zirconium sulfate catalyst is preferred to have acid strength of 11 to 15 ($-H_0$, Hammett indicator). Although there is no particular limit to the precursor of the zirconium sulfate catalyst, preferred is zirconium dichloride oxide $(ZrOCl_2)$.

The zirconium sulfate catalyst may be used alone or otherwise may be supported on a carrier such as alumina, silica, titania, zeolite, or activated charcoal without particular limitation.

Even though the zirconium sulfate catalyst may be used in reactions without pretreatment, the catalyst activity can be increased by treating the catalyst at a temperature of 200 to 700° C. under an inert gas such as hydrogen, nitrogen, helium, or argon. If the temperature is lower than 200° C., water and impurities on the surface of the catalyst cannot be effectively eliminated. On the other hand, if the temperature is higher than 700° C., decomposition of the zirconium sulfate catalyst occurs, thereby decreasing a reaction activity.

In embodiments of the present invention, production of tetrahydrofuran from 1,4-butanediol preferably utilizes 0.1 to 20% by weight of the zirconium sulfate catalyst. If the amount of the zirconium sulfate catalyst is lower than 0.1% by weight, an insufficient amount of catalyst results in deterioration of reaction efficiency. On the other hand, if the amount of the zirconium sulfate catalyst is higher than 20% by weight, an excessive amount of catalyst results in waste of the catalyst.

There is no particular limit to the production method of tetrahydrofuran according to the embodiments of the present invention. For example, tetrahydrofuran may be prepared by the following method. Preparation of tetrahydrofuran from 1,4-butanediol can be carried out by using a liquid- or gas-phase reactor.

When it is desired to employ a gas-phase fixed-bed reactor, 1 to 10 g of a zirconium sulfate catalyst is charged to a fixed-bed tubular reactor and the catalyst is activated with the flow of inert gas at a temperature of 200 to 700° C. Thereafter, 1,4-butanediol is flowed in conjunction with inert gas at a reaction temperature of 150 to 350° C. and a liquid hourly space velocity (LHSV) of 3 to 10.

When it is desired to employ a liquid-phase slurry reactor, 0.1 to 20% by weight of the zirconium sulfate catalyst activated at a temperature of 200 to 700° C. and 1,4-butanediol are charged to the liquid-phase reactor and the reactants are heated to a reaction temperature of 150 to 350° C.

The reaction temperature is preferably in a range of 150° C. to 350° C., and more preferably 200° C. to 270° C. The reaction efficiency is high in the above-specified temperature range. A temperature of less than 150° C. leads to poor reaction, whereas a temperature exceeding 350° C. leads to thermal decomposition of tetrahydrofuran, thereby resulting in deterioration of the selectivity.

Hereinafter, the tetrahydrofuran production process according to the embodiments of the present invention will be described in more detail with reference to FIG. 1.

As shown briefly in FIG. 1, 1,4-butanediol is introduced into a reactor filled with a zirconium sulfate catalyst and is converted into tetrahydrofuran (THF) after a certain period of time. The reaction product obtained in the reactor comprises tetrahydrofuran, water and 1,4-butanediol, and unreacted 1,4-butanediol is recycled to the reactor through a separator (e.g. a distillation column). The mixture passed through the separator, which consists of tetrahydrofuran and water, is analyzed by gas chromatography. In the commercial 1,4-butanediol dehydration process, an azeotropic mixture of water and THF is passed through the separator again, thereby obtaining high-purity tetrahydrofuran having a water content of less than 500 ppm.

The product passed through the reactor in the above production process is composed mainly of unreacted 1,4-butanediol, THF, and water. Only 1,4-butanediol components among these materials are distilled/separated by difference of the boiling points therebetween (THE: 67° C., water: 100° C., and 1,4-butanediol: 230° C.) in a primary separator heated to 110° C. and are recycled to the reactor, and the remaining THF and water are subjected to gas chromatography analysis.

EXAMPLES

Now, the present invention will be described in more detail with reference to the following examples. These examples are provided only for illustrating the present invention and should not be construed as limiting the scope and spirit of the present invention.

Example 1

The gas-phase catalytic reaction was carried out using a fixed-bed tubular reactor (diameter: 20 mm, length: 520 mm). 2 g of a zirconium sulfate catalyst was charged to the reactor and the catalyst was activated with a flow of helium gas at 370° C. for 2 hours. 1,4-butanediol was introduced with a flow of 0.5 cc/min using a syringe pump and mixed with helium gas, and the mixture was introduced into the reactor at a flow rate of 5.0 L/h. The reaction was carried out at 200° C. under atmospheric pressure. The reaction product was analyzed on-line using gas chromatography equipped with a Porapak QS column and a flame ionization detector (FID). Upon analysis of the product after the reaction has reached a steady-state, the yield of tetrahydrofuran was 99.5%.

Example 2

Liquid-phase catalytic reaction was carried out in a 500 mL three-neck reaction flask equipped with a magnetic stirrer and a reflux condenser. Prior to reaction, a zirconium sulfate catalyst was activated at 370° C. for 2 hours using helium gas. 1 g of the thus-pretreated zirconium sulfate and 100 g of 1,4-butanediol were introduced into a reaction vessel. The reaction was carried out at 200° C. for 1 hour under atmospheric pressure. The reaction product was condensed through a condenser, distilled again to separate unreacted 1,4-butanediol and subjected to gas chromatography analysis as in Example 1. From the analysis result of the reaction product, a yield of tetrahydrofuran was 99.5%.

Comparative Examples 1 to 3

1 g of an acidic alumina catalyst (Comparative Example 1), 1 g of a tungstophosphoric acid (TPA) catalyst as a heteropoly acid (Comparative Example 2), or 1 g of a silica-alumina catalyst (Comparative Example 3) and 100 g of 1,4-butanediol were reacted for 60 min according to the same reaction conditions and manner as in Example 2.

After reactions of Examples 1 and 2 and Comparative Examples 1 to 3, each reaction yield is given in Table 1 below.

TABLE 1

| | Ex. 1 | Ex. 2 | Comp. Ex. 1 | Comp. Ex. 2 | Comp. Ex. 3 |
|---|---|---|---|---|---|
| Catalyst | Zirconium sulfate | Zirconium sulfate | Acidic alumina | TPA | Silica-alumina |
| Reaction yield | 99.5 | 99.5 | 76.1 | 83.4 | 73.2 |

As shown in Table 1, it can be seen that the reaction yield was significantly higher in the reaction using zirconium sulfate as a catalyst, as compared to Comparative Examples 1 to 3 utilizing other catalysts. Therefore, use of the zirconium sulfate catalyst can achieve high-yield production of tetrahydrofuran.

As apparent from the above description, according to the production method of embodiments of the present invention, the use of the zirconium sulfate catalyst enables high-yield production of tetrahydrofuran via a simple and low-risk production process, by simultaneously solving the problems associated with lower reaction yields and the potential risks in the production processes which may occur upon production of tetrahydrofuran.

Although the preferred embodiments of the present invention have been disclosed for illustrative purposes, those skilled in the art will appreciate that various modifications and variations are possible, without departing from the scope and spirit of the invention as disclosed in the appended claims. Accordingly, such modifications and variations are intended to come within the scope of the claims.

What is claimed is:

1. A method for production of tetrahydrofuran (THF) from 1,4-butanediol (BDO) using a zirconium sulfate $(Zr(SO_4)_2 \cdot nH_2O)_4$ catalyst.

2. The method according to claim 1, wherein a reaction temperature is in the range of 150 to 350° C.

3. The method according to claim 1, wherein the zirconium sulfate catalyst is used alone or is supported on a carrier.

4. The method according to claim 1, wherein the zirconium sulfate catalyst is pretreated at a temperature of 200 to 700° C. using an inert gas prior to reaction.

5. The method according to claim 3, wherein the carrier of the zirconium sulfate catalyst is selected from the group consisting of alumina, silica, titania, zeolite and activated charcoal.

* * * * *